United States Patent
Reeder et al.

(10) Patent No.: US 6,861,521 B2
(45) Date of Patent: Mar. 1, 2005

(54) STEREOSELECTIVE TRANSACETALIZATION OF STEROIDAL C-22 ACETONIDE

(75) Inventors: Lisa M. Reeder, Kalamazoo, MI (US); Corey L. Stanchina, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 337 days.

(21) Appl. No.: 10/247,246

(22) Filed: Sep. 19, 2002

(65) Prior Publication Data

US 2003/0088090 A1 May 8, 2003

Related U.S. Application Data

(60) Provisional application No. 60/324,589, filed on Sep. 25, 2001.

(51) Int. Cl.[7] .................................................. C07J 71/00
(52) U.S. Cl. ......................................................... 540/70
(58) Field of Search ........................................... 540/70

(56) References Cited

U.S. PATENT DOCUMENTS 5,939,409 A    8/1999  Andersson et al. ......... 514/174

FOREIGN PATENT DOCUMENTS

EP           0 262 108       3/1988

*Primary Examiner*—Brenda Coleman
(74) *Attorney, Agent, or Firm*—James M. Warner; Brandon Boss; John H. Engelmann

(57) ABSTRACT

The present invention is a process for the preparation of rofleponide of formula (II)

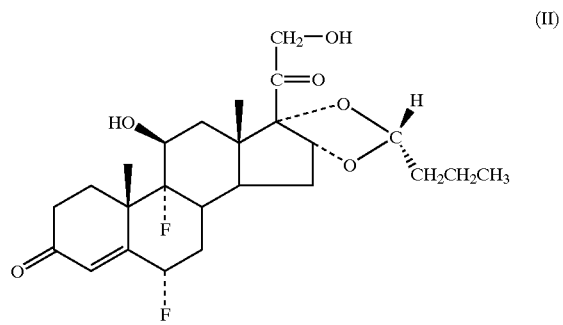

where the 22R/22S ratio is 90/10 or greater which comprises contacting an acetonide of formula (I)

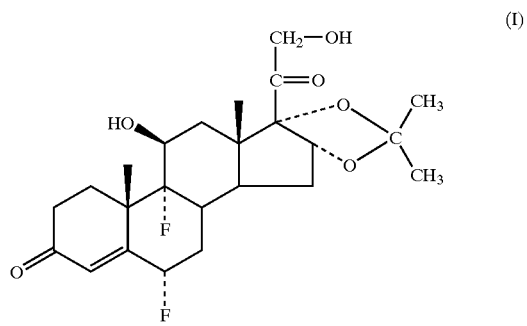

with $CH_3$—$CH_2$—$CH_2$—CHO (III) in the presence of perchloric acid where the concentration of the acetonide (I) is from about 1 g/20 ml to about 1 g/50 ml in the absence of an inert material.

6 Claims, No Drawings

STEREOSELECTIVE TRANSACETALIZATION OF STEROIDAL C-22 ACETONIDE

CROSS-REFERENCE TO RELATED APPLICATIONS

This application claims the benefit of U.S. provisional application Ser. No. 60/324,589 filed on 25 Sep. 2001, under 35 USC 119(e)(i).

BACKGROUND OF THE INVENTION

1. Field of the Invention

The present invention is a process for the transformation of a known steroidal acetonide (I) intermediate to rofleponide (II). Rofleponide (II) is known to be useful as a pharmaceutical agent.

2. Description of the Related Art

U.S. Pat. No. 5,939,409 discloses rofleponide (II) and its use as a glucocorticosteroid useful in treating inflammatory, allergic or immunologic diseases of the respiratory airways (asthma, rhinitis), in skin (eczema, psoriasis) or bowel (ulcerative colitis, Morbus Crohn).

U.S. Pat. No. 5,939,409 discloses the acetonide (I) to be a useful intermediate in the production of rofleponide.

U.S. Pat. No. 5,939,409 discloses a transacetalization process of the acetonide (I) to rofleponide (II). The transacetalization process of U.S. Pat. No. 5,939,409 produces rofleponide (II), but requires the use of small grains of an inert material to prevent a big sticky lump from forming, see column 4, lines 1–9. The process of the present invention does not require the use of an inert material.

European Patent Application 0 262 108 discloses the transacetalization of acetonide (I) to rofleponide (II) but requires the use of small grains of an inert material. The process of the present invention does not require the use of an inert material.

SUMMARY OF INVENTION

Disclosed is a process for the preparation of rofleponide of formula (II)

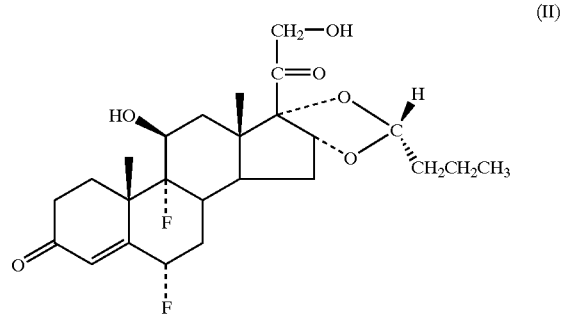

where the 22R/22S ratio is 90/10 or greater which comprises:

(1) contacting an acetonide of formula (I)

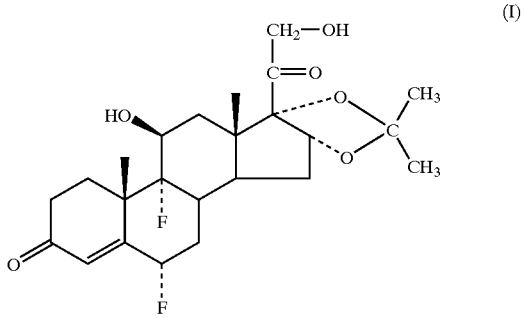

with $CH_3$—$CH_2$—$CH_2$—CHO (III) in the presence of perchloric acid where the concentration of the acetonide (I) is from about 1 g/20 ml to about 1 g/50 ml in the absence of an inert material.

DETAILED DESCRIPTION OF THE INVENTION

Rofleponide (II) and its ester rofleponide palmitate are known to be useful pharmaceutical agents. One method of synthesis of rofleponide (II) is set forth in U.S. Pat. No. 5,939,409. In that patent, the acetonide, 6α,9α-difluoro-11β, 21-dihydroxy-16α, 17α-(isopropylidenedioxy)pregn-4-ene-3–20 dione (I) is transformed to rofleponide (II).

One of the problems in the transacetalization of the acetonide (I) to rofleponide (II) is the low ratio of the 22R/22S epimers. Another problem reported was that when hydrocarbon solvents were used the mixture became a "sticky ball". The prior art also discloses the use of methylene chloride as an operable solvent. The problem of the low epimer ratio has been overcome by use of inert grain materials such as sand, glass and ceramic and inert stainless steel or tantalum, see U.S. Pat. No. 5,939,409 and European Patent Application 0 262 108. However, use of these inert agents on a commercial scale is not feasible. The process of the invention does not require an inert grain material or inert stainless steel or tantalum.

The process of the present patent application is set forth in EXAMPLEs 1 thru 3. Briefly, the starting acetonide, 6α,9α-difluoro-11β,21-dihydroxy-16α,17α-(isopropylidenedioxy)pregn-4-ene-3–20 dione (I) is dissolved in a solvent such as methylene chloride at a concentration of from about 1 g/20 ml to about 1 g/50; it is preferred that the concentration be about 1 g/20 ml. Butyraldehyde, preferably about three equivalents, is added. Next an acid such as perchloric acid is added and the mixture stirred at 20–25° until complete (as measured by TLC or HPLC). No inert material is used. The inert materials used in the prior art, which are not used here include sand, glass, ceramic, silica gel, celite, acid resins and granulated stainless steel or tantalum.

Definitions and Conventions

The definitions and explanations below are for the terms as used throughout this entire document including both the specification and the claims.

I. Conventions

In chemical structural formulas depicting such compounds, a substituent ($X_1$) which is "below" another substituent ($X_2$) will be identified as being in the alpha (α)

configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta (β) configuration and is indicated by an unbroken line attachment to the carbon atom.

II. Definitions

All temperatures are in degrees Celsius.

TLC refers to thin-layer chromatography.

HPLC refers to high pressure liquid chromatography.

Chromatography (column and flash chromatography) refers to purification/separation of compounds expressed as (support, eluent). It is understood that the appropriate fractions are pooled and concentrated to give the desired compound(s).

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

Rofleponide refers to the compound of the formula:

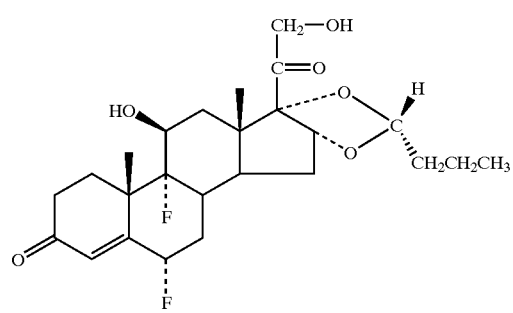

(II)

with the following chemical name, 16α,17α-[(R) butylidenedioxy]-6α,9α-difluoro-11β,21-dihydroxypregn-4-ene-3,20-dione (II).

The acetonide (I) has the following chemical name, 6α,9α-difluoro-11β,21-dihydroxy-16α,17α-(isopropylidenedioxy)pregn-4-ene-3–20 dione.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

16α,17α-[(R)butylidenedioxy]-6α,9α-difluoro-11β, 21-dihydroxypregn-4-ene-3,20-dione (II)

6α,9α-Difluoro-11β,21-dihydroxy-16α,17α-(isopropylidenedioxy)pregn-4-ene-3–20 dione (I, 30 g, 0.066 moles) is dissolved in methylene chloride (500 mL) at 20–25° and then butyraldehyde (17.8 mL, 0.198 moles) is added. Perchloric acid (31.8 mL, 0.528 mol) is quickly added and after 10–15 minutes a precipitate forms. Stirring is continued under nitrogen at 20–25° for 4.5 hr. After this time water (225 mL) is added and stirring continued until all of the solids have gone into solution. The phases are separated and the organic phase is washed with water (2×225 mL). The title compound is obtained, NMR (CDCl$_3$; 400 MHz )6.24, 5.44–5.40, 5.33–5.28, 5.03, 5.01, 4.71, 4.70, 4.69, 4.65, 4.60, 4.50–4.48, 4.39, 4.34, 2.70–2.45, 2.45–2.30, 2.30–2.20, 2.05–1.93, 1.90–1.93, 1.90–1.76, 1.61, 1.56–1.50, 1.05, 1.03, 1.01 and 0.99δ.

HPLC analysis of the methylene chloride mixture shows the ratio of R/S epimers is 98/2. HPLC conditions are: column is Phenomenex Prodigy 5μ ODS-3V, C-18, 250×4.6 mm; mobile phase is water/ethanol (40/60); flow rate is 0.7 mL/min; run time is 15.00 mm; the detector is 234 nm and the injector volume is 5 μL.

Example 2

16α,17α-[(R)butylidenedioxy]-6α,9α-difluoro-11β, 21-dihydroxypregn-4-ene-3,20-dione (II)

6α,9α-Difluoro-11β,21-dihydroxy-16α,17α-(isopropylidenedioxy)pregn-4-ene-3–20 dione (I, 100 g, 0.22 moles) is dissolved in methylene chloride (2.5 L) at 20–25° and then butyraldehyde (47.6 mL, 0.66 moles) is added. Perchloric acid (55.8 mL, 0.92 mol) is quickly added and after 10–15 minutes a precipitate forms. Stirring is continued under nitrogen at 20–25° for 4 hr. After this time an aqueous sodium bicarbonate solution (12%, 500 mL) is added and stirring continued until all of the solids have gone into solution. The phases are separated and the organic phase is washed with water (2×500 mL). HPLC analysis of the methylene chloride mixture shows the ratio of R/S epimers is 95/5.

Example 3

16α,17α-[(R)butylidenedioxy]-6α,9α-difluoro-11β, 21-dihydroxypregn-4-ene-3,20-dione (II)

6α,9α-Difluoro-11β,21-dihydroxy-16α,17α-(isopropylidenedioxy)pregn-4-ene-3–20 dione (I, 5 g, 0.011 moles) is dissolved in methylene chloride (80 mL) at 20–25° and then butyraldehyde (3.0 mL, 0.033 moles) is added. Perchloric acid (5.0 mL, 0.082 mol) is quickly added and after 10–15 minutes a precipitate forms. Stirring is continued under nitrogen at 20–25° for 1 hr. After this time water (80 mL) is added and stirring continued until all of the solids have gone into solution. The phases are separated and the organic phase is washed with water (2×100 mL). HPLC analysis of the methylene chloride mixture shows the ratio of R/S epimers is 98/2.

CHART A

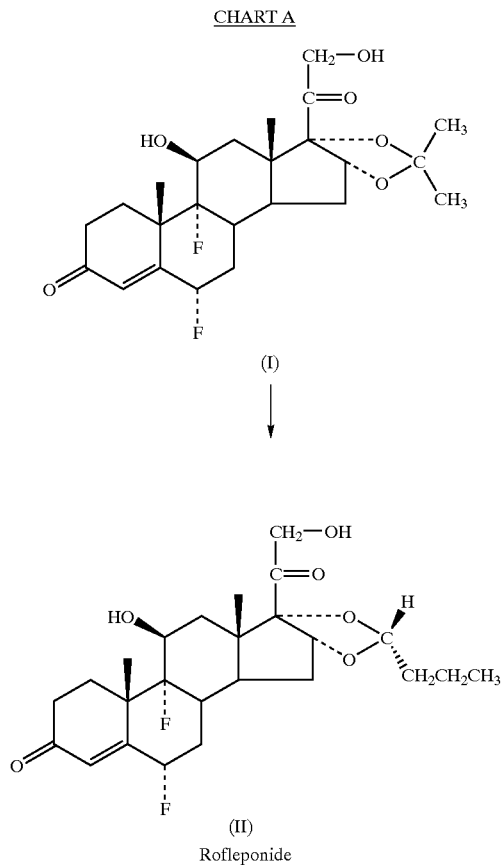

Rofleponide

What is claimed is:

1. A process for the preparation of rofleponide of formula (II)

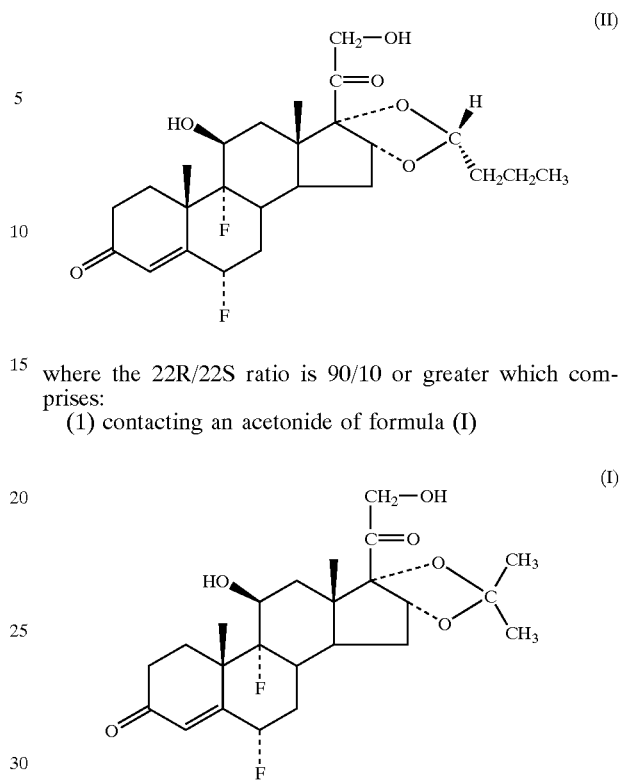

where the 22R/22S ratio is 90/10 or greater which comprises:

(1) contacting an acetonide of formula (I)

with $CH_3-CH_2-CH_2-CHO$ (III) in the presence of perchloric acid where the concentration of the acetonide (I) is from about 1 g/20 ml to about 1 g/50 ml in the absence of an inert material.

2. A process according to claim 1 where the 22R/22S ratio is 95/5 or greater.

3. A process according to claim 2 where the 22R/22S ratio is about 97/3.

4. A process according to claim 1 where the process uses methylene chloride as the solvent or co-solvent.

5. A process according to claim 1 where the process is performed in the absence of an epimeric modifier.

6. A process according to claim 1 where the concentration of the acetonide (I) is about 1 g/20 ml.

* * * * *